United States Patent [19]

Russell

[11] Patent Number: 5,239,354
[45] Date of Patent: Aug. 24, 1993

[54] METHOD AND APPARATUS FOR THE POSITIVE IDENTIFICATION OF A NATURAL PEARL AND FOR MEASURING THE THICKNESS OF THE NACRE COATING OF CULTURED PEARLS

[76] Inventor: Kenneth M. Russell, 4512 Avamere St., Bethesda, Md. 20814

[21] Appl. No.: 941,175

[22] Filed: Sep. 4, 1992

Related U.S. Application Data

[63] Continuation-in-part of Ser. No. 717,663, Jun. 19, 1991, Pat. No. 5,146,288.

[51] Int. Cl.$^5$ .................. G01N 21/87; G01B 11/06
[52] U.S. Cl. ........................................ 356/30; 356/381
[58] Field of Search ................... 356/30, 381, 382, 73

[56] References Cited

U.S. PATENT DOCUMENTS 4,906,083 3/1990 Sattler .................................. 356/30

FOREIGN PATENT DOCUMENTS

| 68126 | of 1926 | Australia | 356/30 |
|---|---|---|---|
| 421449 | 10/1924 | Fed. Rep. of Germany | 356/30 |
| 458813 | 3/1928 | Fed. Rep. of Germany | 356/30 |
| 592529 | 10/1925 | France | 356/30 |
| 606373 | 6/1926 | France | 356/30 |
| 56-61635 | 5/1981 | Japan | 356/30 |
| 183674 | 8/1922 | United Kingdom | 356/30 |
| 253373 | 6/1926 | United Kingdom | 356/30 |

OTHER PUBLICATIONS

*Olympus Measuring Microscopes*, STM5/STM5-MJS/STJ, p. 11, Olympus Optical Company, Lake Success, N.Y. undated.
*Edmund Scientific 1992 Annual Reference Catalog For Optics, Science and Education*, pp. 8–10 and 48, Edmund Scientific Company, Barrington, N.J.

Primary Examiner—F. L. Evans
Attorney, Agent, or Firm—Staas & Halsey

[57] ABSTRACT

An apparatus comprising a light source, a lens system, a reticle illuminated by the light source, a housing having a substantially dark viewing chamber and a pearl holder for holding the cultured pearl in the substantially dark viewing chamber, and a reticle device for providing a reticle image observable through the lens system. The substantially dark viewing chamber is optically connected to the light source so as to allow light from the light source to traverse an aperture in the pearl holder to illuminate the pearl. The substantially dark viewing chamber is also optically connected to the lens system. In order to provide maximum contrast between light and darkness in the substantially dark viewing chamber, the housing is arranged to prevent entry of extraneous light into the substantially dark viewing chamber. A preferred method according to the present invention includes the following steps. A pearl is placed in the substantially dark viewing chamber. The pearl is illuminated by irradiating a relatively small portion of a side of the pearl with light from the light source, so that luminescence is stimulated throughout the pearl only when the pearl is a natural pearl, and so that the thickness of the nacre coating is observable through the lens system when the pearl is a cultured pearl. The thickness of the nacre coating of the illuminated pearl is measured by comparison with the reticle image observed through the lens system.

20 Claims, 7 Drawing Sheets

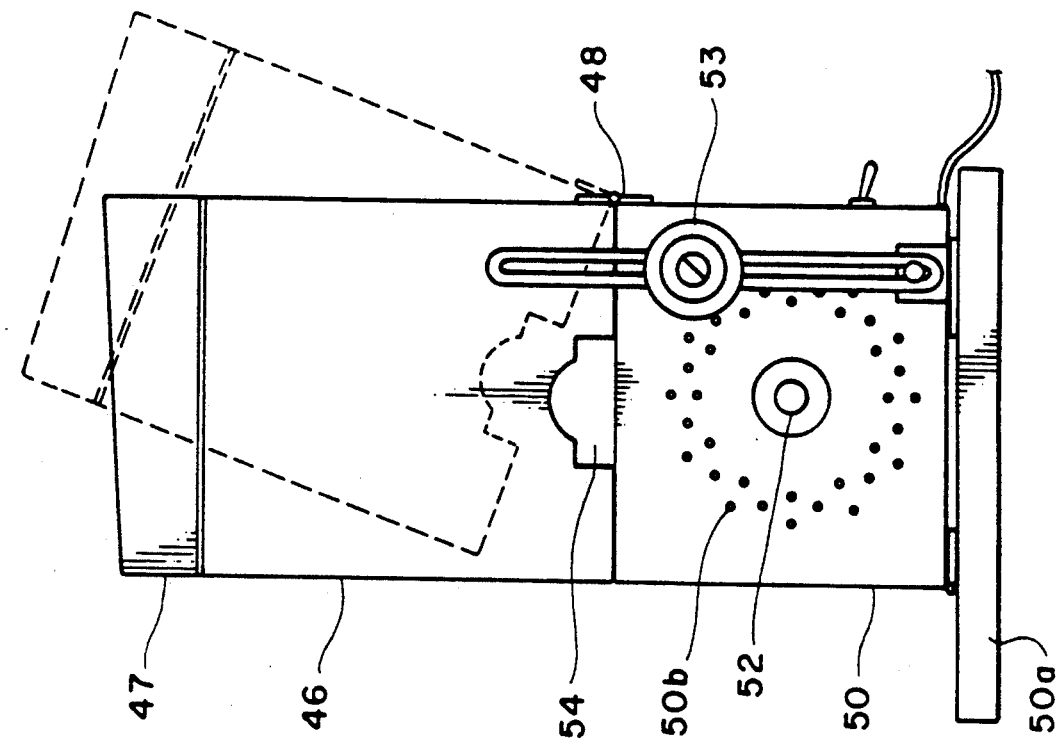
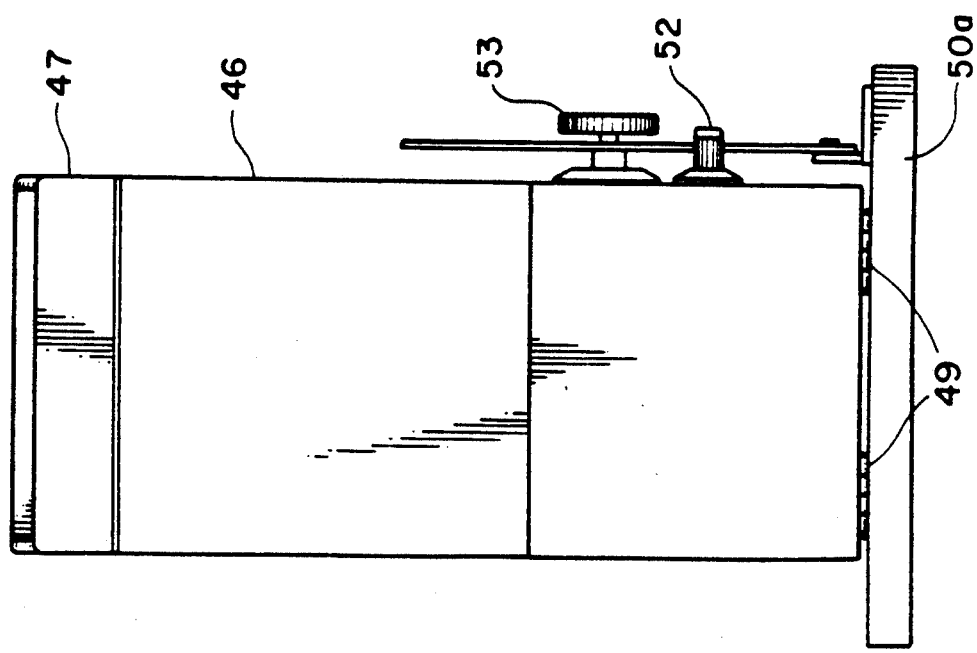

METHOD AND APPARATUS FOR THE POSITIVE IDENTIFICATION OF A NATURAL PEARL AND FOR MEASURING THE THICKNESS OF THE NACRE COATING OF CULTURED PEARLS

RELATED APPLICATIONS

This application is a continuation-in-part of application Ser. No. 07/717,663, filed Jun. 19, 1991, now U.S. Pat. No. 5,146,288.

BACKGROUND OF THE INVENTION

1. Field of the Invention

The present invention relates generally to the examination of pearls and, more particularly, to positively identifying natural pearls, and to measuring the thickness of the nacre coating of cultured pearls.

The jewelry industry's standard manual for identifications declares that the distinction between natural pearls and cultured pearls is the industry's most difficult distinction, even for gem experts, and for lack of any non-destructive alternative, requires X-ray examination by special laboratories. Such an examination may be inconvenient or impossible in many business situations.

Thus, there is widespread general confusion, even among experts, that has endured all of the approximately 100 years since advent of cultured pearls. Most jewelers are aware in a general way of the cultured pearls pretense but find it profitable. Few of today's American customers have any acquaintance with natural pearls. Most have never owned any. Chiefly from estates, there are still in private hands many natural pearls, singly or in necklaces, and these may confront the trader with decisions between a few hundred dollars and thousands.

The United States has imported in a year as much as 500 million dollars worth of cultured pearls and cultured pearl jewelry. Most such pearls are composed of more than 90 percent mother-of-pearl bead made from Mississippi or Tennessee river clamshell that costs about 30 cents per pound. The clamshell beads were found to be compatible material which when surgically inserted into the oyster, caused fewer mortalities of the host mollusks.

Many years ago, pearl culturers worked toward a one-half millimeter addition of nacre (calcium carbonate) as representing good quality cultured pearls. This might require as much as three years of nurture. Many cultured pearls subsequently have been created with only a few months of nurture and, consequently, have a nacre coating of negligible thickness. Often, the nacre coating is so thin that striations of the mother-of-pearl bead can be seen therethrough. Moreover, the reduced thickness of the nacre coating adversely affects the durability of the cultured pearl. The transition of the cultured pearl industry from a confined one of relatively few producers and subject to strict quality controls to one of many producers, some of which market cultured pearls that are too thinly coated with nacre, puts forth serious problems.

As in the distinction between natural pearls and cultured pearls, for lack of any non-destructive alternative, X-ray examination by special laboratories is required to determine the thickness of the nacre coating of cultured pearls. Again, such an examination may be inconvenient or impossible in many business situations.

2. Description of the Related Art

In the past, there have been many efforts and devices to distinguish between natural and cultured pearls. None were practical, convenient and certain.

One such distinguishing method required a hole to be drilled through the pearl. A tiny mirror and light were then inserted, and there might be seen the circular lines of nacre coating. Another method was to measure and compare the specific gravity of a pearl against the known number for natural pearl. It is sometimes suggested that a way to identify cultured pearls in a necklace is to hold the necklace in a straight line on white paper beneath a lamp, then rotate the pearls to observe whether they show a flash when the mother-of-pearl beads reach an aspect at which light is reflected. Flashing would be from the bright plane of individual mother-of-pearl beads and would occur twice in 360 degrees. Inasmuch as the mother-of-pearl beads are drilled at random, such coincidence is chancy. Moreover, this technique offers nothing to positively identify natural pearls. All these and other attempts fall short of anything for widespread use.

The most effective distinguishing method, and still the general last resort, has been X-ray examination. Likewise, X-ray examination can be used to determine the thickness of the nacre coating of a cultured pearl. However, X-ray examination is inconvenient, because it must be performed in special laboratories, which is an impossibility in many business situations.

A cultured pearl may be sawed or ground to expose the thickness of the nacre coating. However, this is a destructive examination procedure and merely measures the thickness of the nacre coating of the destroyed cultured pearl. Similarly, one may drill a hole through a cultured pearl, and examine the circular lines of the nacre coating with a tiny mirror and light inserted into the hole. Again, this is a destructive test and would merely provide a measure of the thickness of the nacre coating of the drilled-through cultured pearl.

Candling has been mentioned repeatedly relative to examining pearls. Candling, or backlighting to see the interior, has long been familiar for the detection of hens eggs with an embryo, to cull these from food marketing. Though candling may provide an identification of a cultured pearl, until the present invention, candling has not permitted accurate measurement of the thickness of the nacre coating of a cultured pearl.

SUMMARY OF THE INVENTION

An object of the present invention is to provide a convenient, non-destructive method and apparatus for positively identifying a natural pearl.

Another object of the present invention is to provide a convenient, non-destructive method and apparatus to accurately measure the thickness of the nacre coating of cultured pearls.

These and other objects of the present invention are achieved by an apparatus comprising a light source, a lens system, a reticle illuminated by the light source, a housing having a substantially dark viewing chamber and a pearl support for holding the cultured pearl in the substantially dark viewing chamber, and a reticle device for providing a reticle image observable through the lens system. The substantially dark viewing chamber is optically connected to the light source so as to allow light from the light source to traverse an aperture in the pearl support to illuminate the pearl. The substantially dark viewing chamber is also optically connected to the lens system. In order to provide maximum contrast between light and darkness in the substantially dark viewing chamber, the housing is arranged to prevent entry of extraneous light into the substantially dark viewing chamber.

A preferred method according to the present invention includes the following steps. A pearl is placed in the substantially dark viewing chamber. The pearl is illuminated by irradiating a relatively small portion of a side of the pearl with light from the light source, so that luminescence is stimulated throughout the pearl only when the pearl is a natural pearl, and so that the thickness of the nacre coating is observable through the lens system when the pearl is a cultured pearl. The thickness of the nacre coating of the illuminated pearl is measured by comparison with the reticle image observed through the lens system.

These and other features and advantages of the present invention will become more apparent with reference to the following detailed description and drawings. However, the drawings and descriptions are merely illustrative in nature and not restrictive.

BRIEF DESCRIPTION OF THE DRAWINGS

In the drawings, like numerals designate like elements.

FIG. 1A shows a cross section of a natural pearl, while FIG. 1B shows a cross section of a cultured pearl having a mother-of-pearl bead made from clamshell;

FIGS. 3A and 3B respectively show a front view and a left side view of the apparatus of FIG. 2;

DESCRIPTION OF THE PREFERRED EMBODIMENT

At the outset, it is important to note that the major features of the preferred embodiment are constructed and arranged to exploit the differences in the appearance of natural and cultured pearls when illuminated, and to permit measurement of the thickness of the nacre coating of cultured pearls.

Natural pearl is shown by the present invention to have a basic structure which, in darkness, accepts an intense light beam striking only a small area of its surface and then redistributes the light to suffuse the entire body and stimulate luminescence, and thereby make the natural pearl glow markedly. Neither cultured nor imitation pearl does this. Only the elements of the present invention reveal this phenomenon.

Figure 1A:
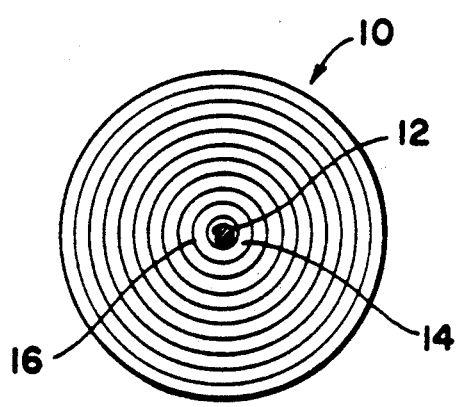
FIGS. 1A and 1B respectively show schematic views of the construction of natural and most cultured pearls. More specifically.
Figure 1B:
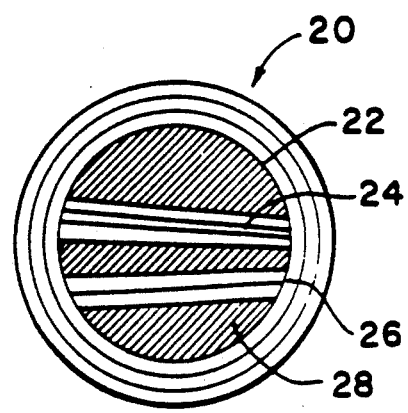

The great disparity between the make-up of the two kinds of pearls is general shown in FIGS. 1A and 1B. FIG. 1A shows a cross section of a natural pearl 10. The natural pearl 10 consists entirely, other than the core irritant 12, of successive overlays 14 of micro platelets of aragonite (calcium carbonate) that have crystallized from nacre and have arranged themselves, without exception, at 90 degrees to an imaginary line from the center of natural pearl 10. The layer lines 16 of overlays 14 are not normally visible because each layer totally envelops the natural pearl 10, leaving no edges. Light striking these platelets at any substantial angle is readily transmitted via a narrowing cone to the center of natural pearl 10. The light is then shunted in all directions excepting the source cone. Hence, the glow previously described.

FIG. 1B shows a cross section of a cultured pearl 20 having a bead 22 made from clamshell which is mother-of-pearl having layer lines 24. By far, the largest proportion of cultured pearls for many years have been made and are presently made, as shown in FIG. 1B, by deceiving the mollusks into adding nacre layers 26 onto bead 22. The invention reveals laminations of such beads as quite straight lines 24 or zones 28. Natural pearls have no such lines or zones. Unlike the natural pearl 10, cultured pearl 20 does not absorb light due to edge blunting of bead 22, plus the dampening effect of much conchiolin. Without light absorption, much of any imposed light goes instead into reflectance, which may account for the shininess of all cultured pearls compared to the "soft" luster of natural pearls.

Figure 2:
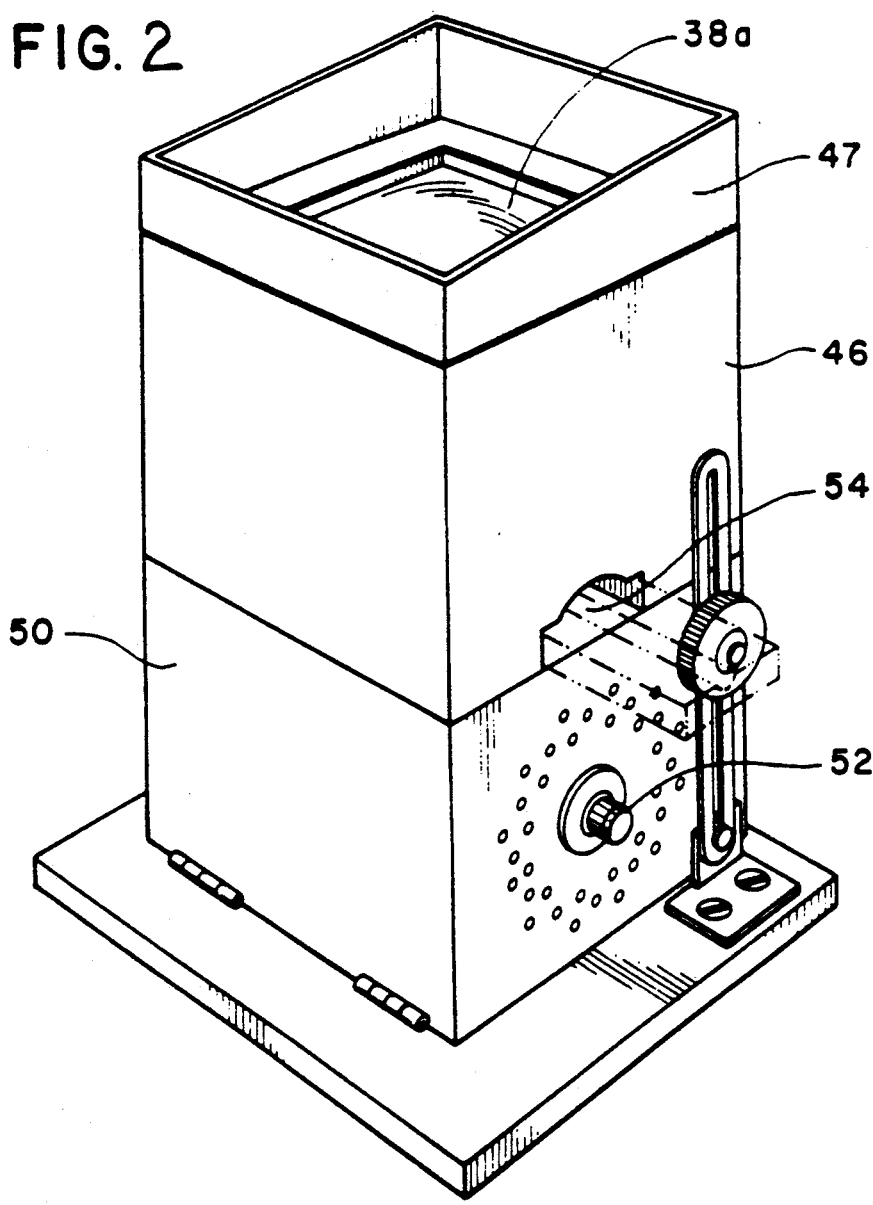
FIG. 2 shows an overall view of an embodiment according to the present invention.
Figure 4:
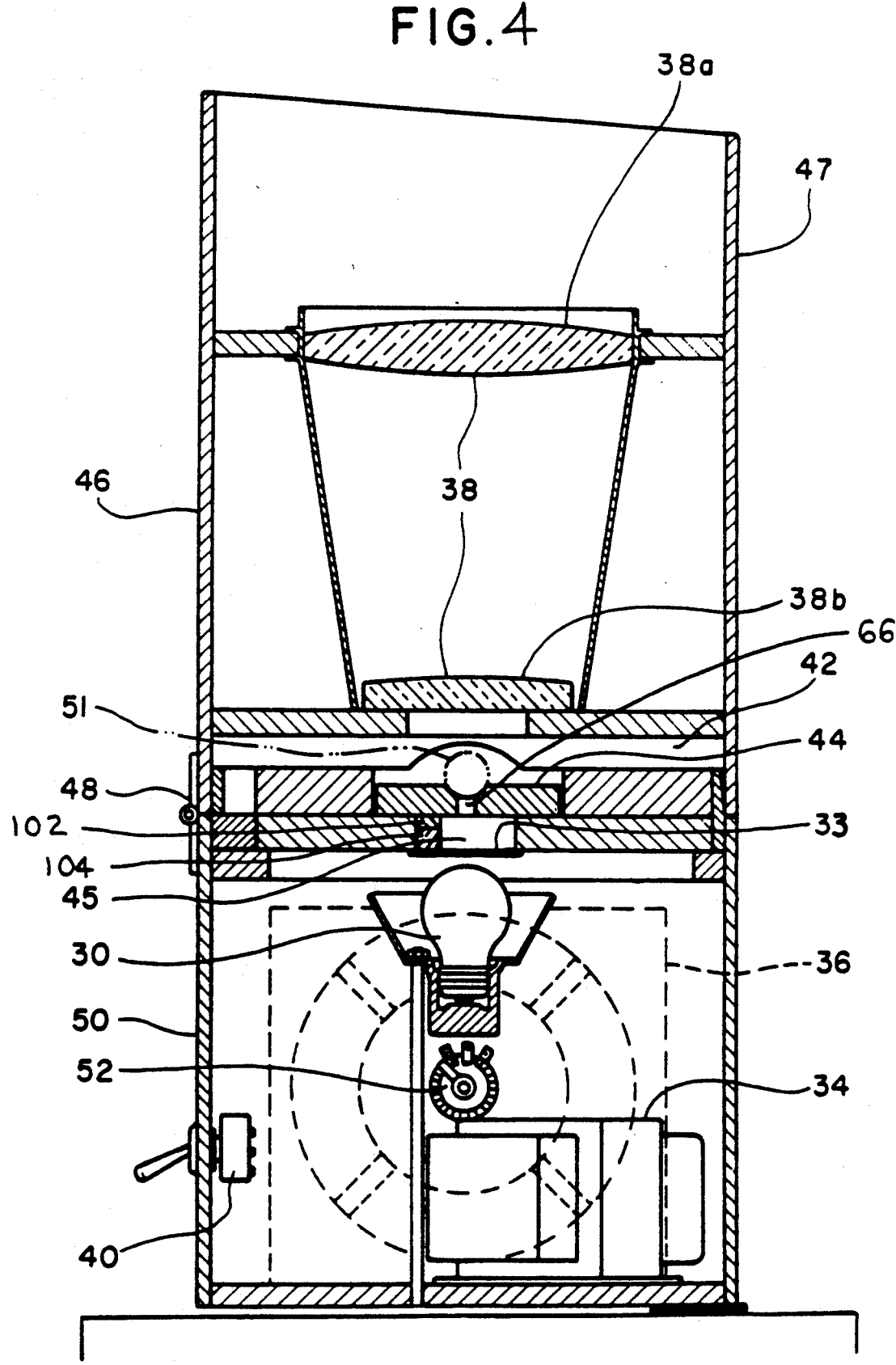
FIG. 4 shows a cutaway right side view of the apparatus of FIG. 2.

FIG. 2 shows an overall view of an embodiment according to the present invention, while FIGS. 3A and 3B respectively show a front view and a left side view of the apparatus of FIG. 2. FIG. 4 shows a cutaway right side view of the apparatus of FIG. 2.

As best seen in FIG. 4, the apparatus comprises an intense light source 30 of, for example, about 28 watts, preferably with a polarizing filter 33, as well as a step-down transformer 34 (e.g., 3.0A, 6.3-0-6.3V), a cooling fan 36 (e.g., 115V, 2A, brushless fan), a direct magnifying lens system 38 having magnifying lenses 38a,38b, an on-off switch 40, a 115 AC voltage intake (not shown), a dark chamber 42, and a pearl holder 44. The apparatus comprises two separable boxes, an upper box 46 hinged by an upper hinge 48 to a lower box 50. Alternatively, upper box 46 may slide into and out of engagement with lower box 50. The lower box 50 has a bore 45 for providing light from light source 30 into dark viewing chamber 42. The upper box 46 has a hood extension 47 to prevent entry of extraneous light into dark viewing chamber 42 and contains the direct magnifying lens system 38. The lower box 50 contains the lighting system to illuminate pearls 51 placed near the top of lower box 50. Any sort of intense lighting system would do. Preferably, the apparatus has a dimmer switch 52 (e.g., 15Ω, 0.01A, rheostat) to minimize any eyestrain on the user if maximum power is not needed.

Preferably, the light source 30 is an incandescent bulb of about 28 watts powered indirectly from a usual 115 volt AC outlet, for convenience. The direct power supply could be from a stepdown transformer 34 in the lower box 50, producing 12 volts, for example. An on-off power switch 40 and a cooling fan 36 are preferably included.

As best seen in FIGS. 3A and 3B, lower box 50 may be attached to a base 50a by forward tilt hinges 49, and the angle of lower box 50 relative to base 50a may be adjusted by forward tilt adjuster 53. Lower box 50 also includes air exhaust vent 50b.

Referring back to FIG. 4, a pearl holder 44 to position pearls 51 in line with the light beam through bore 45 and lens system 38 is placed near the top of lower box 50 and may rest upon it. Pearl holder 44 is accessible by lifting upper box 48. Or, as shown in FIG. 2, the viewing site may be accessed by slides (shown in phantom lines) of opaque plastic or other material, carrying target pearls, through slots 54 that may be cut into the lower edge of the sides of said upper box 46.

Figure 5B:
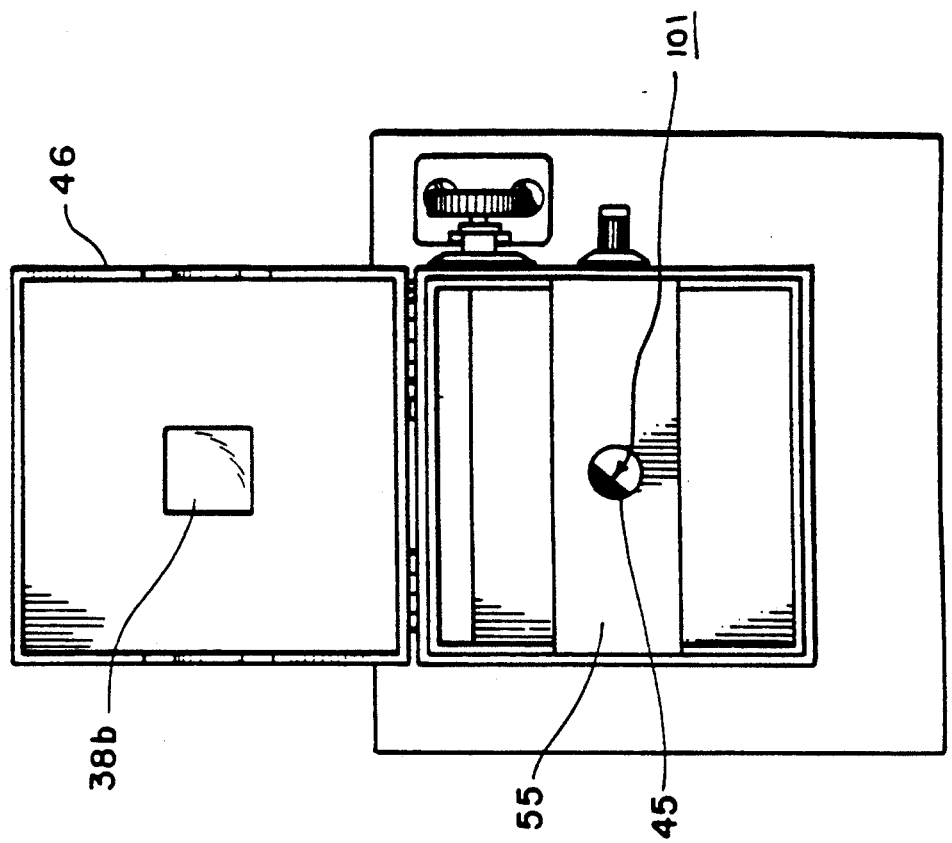
FIGS. 5A and 5B show top views of the apparatus of FIG. 2 with its top closed and open, respectively.
Figure 5A:
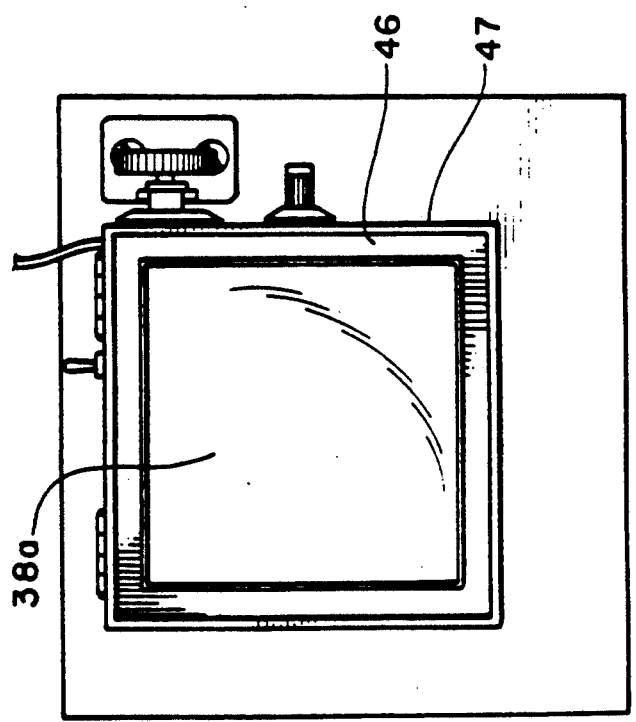

As best shown in FIG. 5B, the slides move through a slide channel 55 provided on the upper portion of lower box 50. Slide channel 55 may have a width of about 1.5 inches (38.1 mm), for example. Bore 45 is disposed at the bottom of slide channel 55, and may have a diameter of about 1 inch (25.4 mm), for example.

Figure 6:
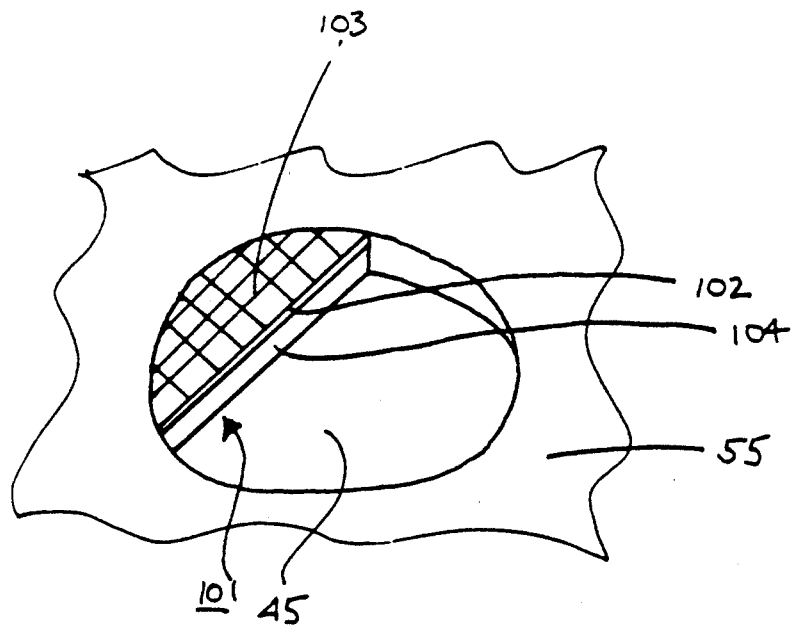
FIG. 6 shows an enlarged overall view of the bore area of the apparatus of FIG. 2.

FIG. 6 is an enlarged overall view of reticle 101. Reticle 101 includes a grid film 102 having grid lines 103 of known dimensions. Preferably, grid film 102 is a photo film which is positively developed to form grid lines 103, each having 0.01-1.0 mm sides, for example. Preferably, the side of each grid is 0.5 mm. Grid film 102 may be produced by, for example, photographing engineering graph paper and reducing the positive photo film to 50%. Reticle 101 also includes a light reducing film 104. Preferably, light reducing film 104 is Plexiglas ® No. 2370 Bronze made by Rhom & Haas Company, Independence Mall, West Philadephia, Penna. Light reducing film 104 greatly reduces the power and glare of the light emitted therethrough from light source 30.

Referring back to FIG. 5B, if the front of the apparatus is considered as six o'clock, reticle 101 is mounted at ten o'clock in bore 45. Reticle 101 occupies about one-third of bore 45, but does not encroach upon the portion of the light from light source 30 which passes through an aperture 66 for illuminating pearl 51. The arcuate portion of the sector-shaped reticle is attached to the edge of bore 4 with adhesive cement, for example. Although reticle 101 is discussed above as being positioned at ten o'clock in bore 45, other positions both within bore 45 and outside bore 45 are possible.

Figure 7B:
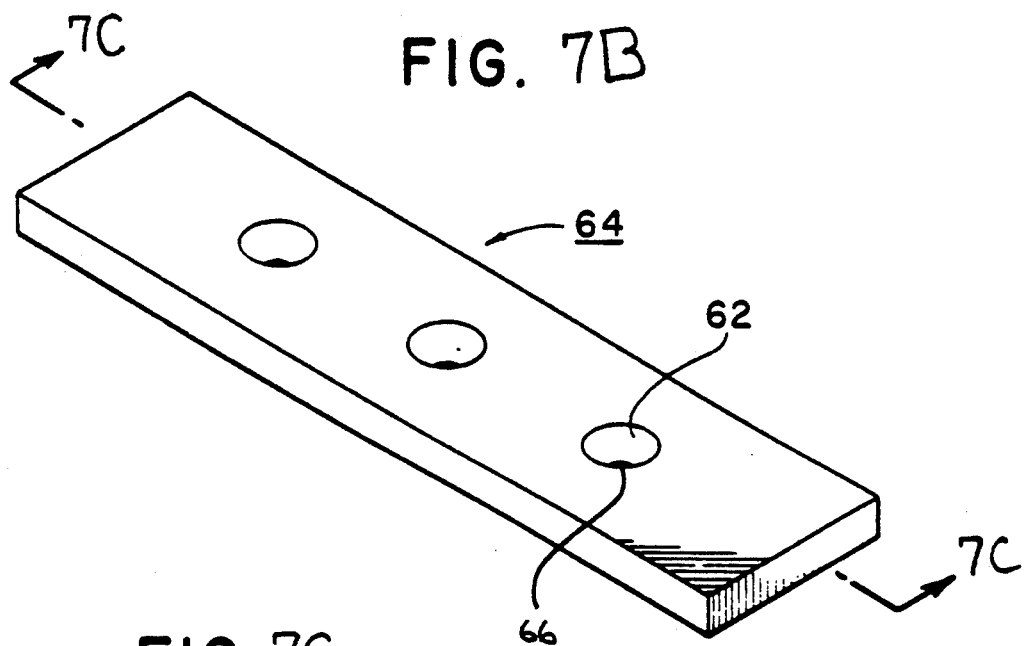
FIGS. 7B and 7C respectively show an overall view and a cutaway side view of a first slide tray that may be used as a holder.
Figure 7C:
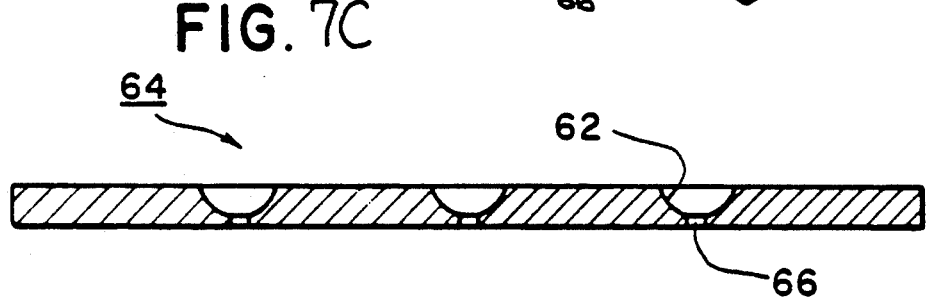
Figure 7A:
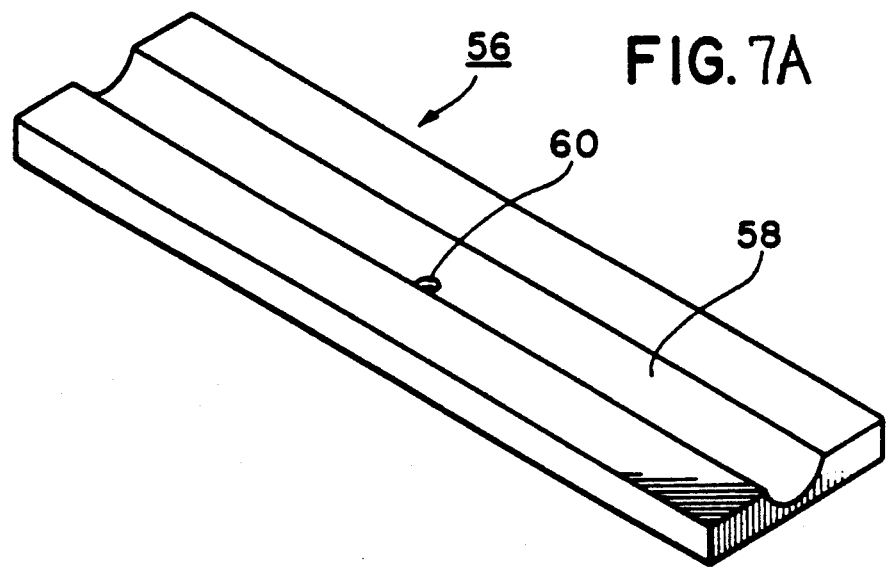
FIG. 7A shows an overall view of a second slide tray that may be used as a holder.

The slides may be of various design. For example, as shown in FIG. 7A, a slide 56 may be grooved from end to end to form a rounded trough 58 for a string of pearls to rest on, with small apertures 6 drilled vertically at several points through the bottom of the trough to admit a beam of light. Slide 56 does not make reticle 101 visible to lens system 38. Or, as shown in FIGS. 7B and 7C, there may be rounded craters 62 spaced at intervals along the center line of a slide 64 with an aperture 66 cut through the base of each of said craters 62 to admit the light beam. Like slide 56, slide 64 does not make reticle 101 visible to lens system 38. Other configurations are possible, so long as they achieve the basic purpose of fixing the target pearl over the intense light and directly below the line of sight of the user.

Figure 7D:
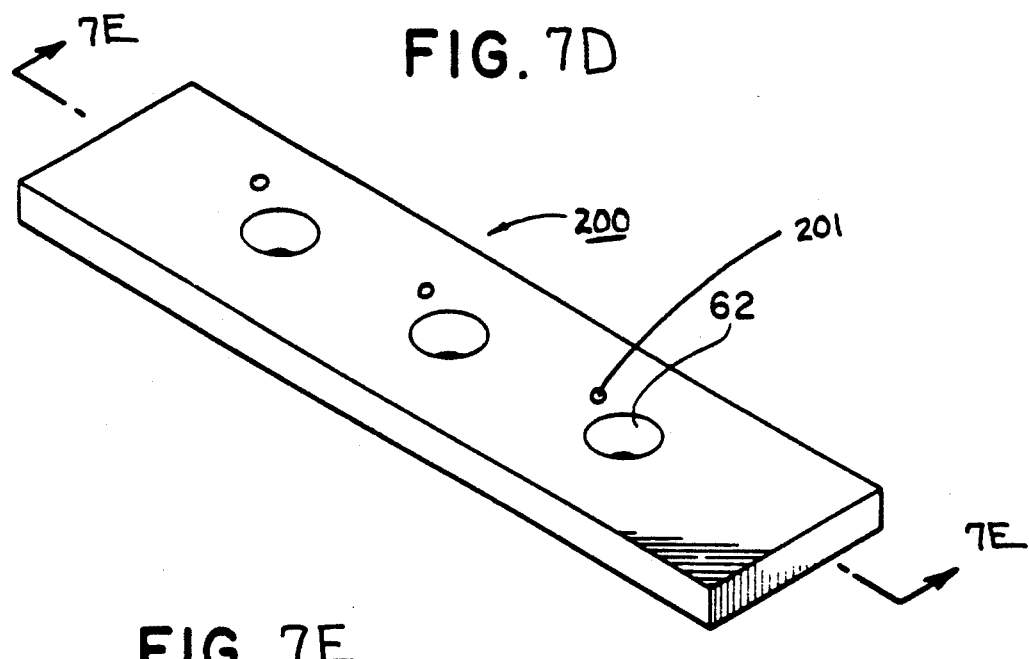
FIGS. 7D and 7E respectively show an overall view and a cutaway view of a third slide tray that may be used as a holder and which includes a reticle aperture.
Figure 7E:
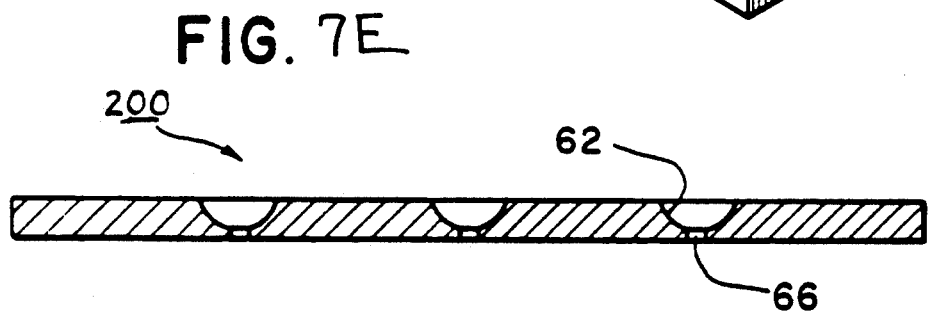

FIGS. 7D and 7E respectively show an overall view and a cutaway view of a slide 200, which is exactly like slide 64, but for the presence of a reticle aperture 201 adjacent to each aperture 66. Alternatively, reticle aperture 201 may be provided with a slide having a trough arrangement similar to that shown in FIG. 7a, for receiving a string of pearls. The reticle aperture 201 is coincident with reticle 101 so that a reticle image is observable from lens system 38. Reticle aperture 201 may be a 1/16 inch (1.6 mm) round hole drilled vertically at a position of ten o'clock about 8 mm outward from the center of aperture 66. Alternatively, reticle aperture 201 may be located anywhere within the field of view of lens system 38 so long as reticle aperture 201 is coincident with reticle 101. Also, reticle 101 may be illuminated by a separate light source. For example, reticle 101 may be illuminated by a low intensity light source so as to remove the need for light reducing film 104.

The apertures 60 and 66 should not be large, preferably not more than 1/16 to ⅛ inch (1.6 mm-3.2 mm). Of course, any lighting apparatus that can also hold a pearl between the light beam and the viewing lens can work in some degree, but it is the strong polarized beam combined with virtually complete darkness that sets the stage for measurement of the nacre coating of a cultured pearl and the stage for the natural pearl to dramatically declare itself by the glowing effect absent in cultured or imitation pearls.

The polarized filter 33 does two things. It narrows the applied beam to eliminate scattered light that would mar the darkness, and it makes the magnified images sharper. It is helpful, but perhaps not entirely essential.

Figure 8:
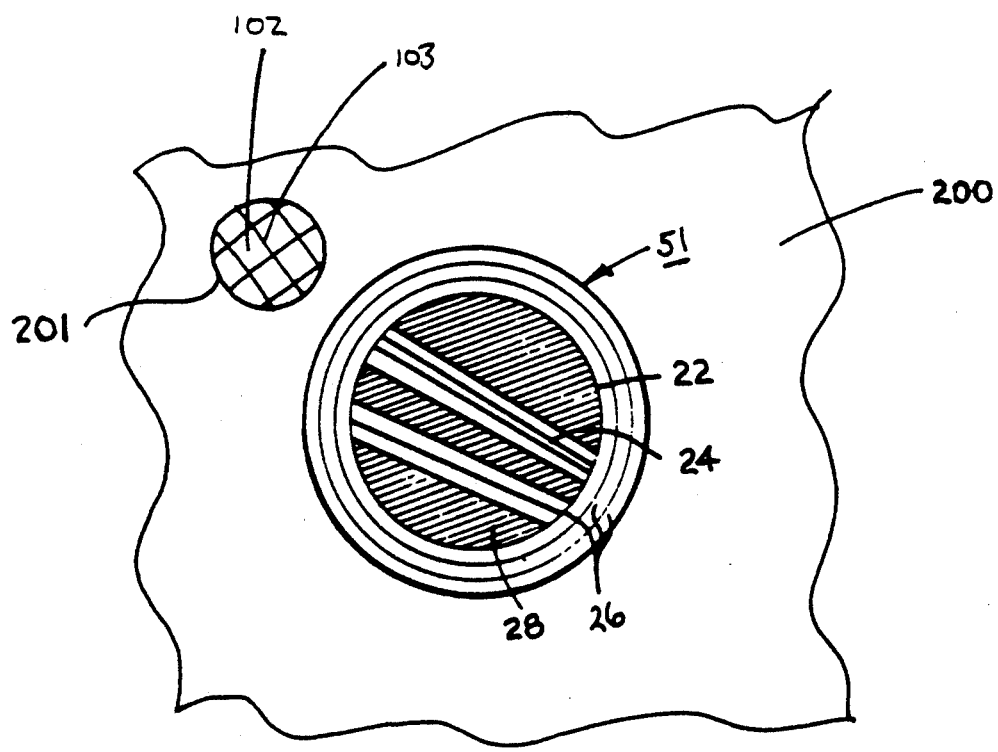
FIG. 8 is a representation of the view of a cultured pearl and the reticle through the lens system of the apparatus of FIG. 2.

FIG. 8 is a representation of the view through lens system 38 when slide 200 is used to measure the thickness of the nacre coating of a cultured pearl. Because pearl 51 is illuminated in dark viewing chamber 42, the nacre layers 26 are observable. The thickness of the nacre coating is seen as a profiled maximum radial separation of two concentric and transluscent spheres, i.e., the outside of bead 22 and the outside of pearl 51. The image of reticle 101 is also illuminated in dark viewing chamber 42 through aperture 201. The observed thickness of the nacre coating of pearl 51 is visually measured by comparison with the grid lines 103 of reticle 101. Preferably, pearl 51 is positioned on crater 62 so that the end of striation lines 24 of bead 22 is in view, since this makes the outside of bead 22 even more apparent.

The user, by repeated visual comparison, judges the thickness of the nacre coating relative to the grid squares of reticle 101. For example, if the thickness of the nacre coating of the cultured pearl appears to be one-fifth of a side of a grid of reticle 101, and each grid has a 0.5 mm side, the thickness of the nacre coating is calculated to be about 0.1 mm.

Working with such small dimensions, it is preferable that lens system 38 provide parallel enlargement of about 5× to 10× in order to make the measurement reasonably efficient. According to the embodiment shown, the pearl is closer to lens system 38 than is reticle 201, which creates a sightly high measurement. However, this error is negligible, and not more than 10%. Alternatively, reticle 101 can be placed on a projection from slide 200 so as to be at the same level relative to lens system 38 as the pearl. For example, reticle 101 may be attached to the end of an optical fiber projected from slide 200.

Instead of direct scale application, the above-described embodiment uses repeated alternative consideration of the separated reticle image and illuminated pearl in successive visual estimate comparisons. However, the present invention may be modified to incorporate direct scale application.

Also, although the present invention describes a backlit reticle using a grid film, the present invention may be modified to use various other types of illuminated reticles. For example, a backlit LCD may be used to form the reticle image. Similarly, LED elements or laser beams may be used to form the reticle image.

The invention may be modified to use various other types of reticles to produce a reticle image on the illuminated pearl. However, because the measurement involves the curved surface of a pearl, and because each pearl is a different size, such reticles appear less practical. Contact reticles, i.e., those that physically lay their scales on top of the subject, might theoretically be used. However, placement of such a contact reticle on the subject pearl would be difficult. Moreover, because the distance between the lens system and the contact reticle would change with the varied size of the pearl, a more complicated lens system with extensive focus adjustment would be required. Also, the scale of the contact reticle will change with the varied distance. Non-contact reticles, i.e., reticles in an objective lens or in an eyepiece, might also theoretically be employed. Such non-contact reticles require a precise positioning of the portion of the pearl to be measured, and such positioning would be almost impossible because pearls of various sizes are to be examined.

Numerous modifications and adaptations of the present invention will be apparent to those skilled in the art. For example, although the embodiment discussed above uses a reticle having square grids, other arrangements and scales may be used. Thus, it is intended by the following claims to cover all modifications and adaptations which fall within the true spirit and scope of the invention.

What is claimed is:

1. An apparatus for measuring the thickness of the nacre coating of a cultured pearl, comprising:
   a light source;
   a lens system;
   a housing having a substantially dark viewing chamber and a pearl holder for holding a cultured pearl in said substantially dark viewing chamber, said substantially dark viewing chamber being optically connected between said light source and said lens system, said housing being arranged to prevent entry of extraneous light into said substantially dark viewing chamber, said pearl holder having an aperture arranged to allow light from said light source to illuminate said cultured pearl; and
   reticle means for providing a reticle image observable through said lens system.

2. An apparatus as recited in claim 1, further comprising:
   a polarization filter located between said light source and said pearl holder, said polarization filter polarizing light from said light source.

3. An apparatus as recited in claim 2, wherein:
   said aperture is about 1.6 to 3.2 mm in diameter.

4. An apparatus as recited in claim 1, wherein:
   said housing includes a left side wall, a right side wall, and front and back walls, and has slots placed in said left and right side walls, said left and right side walls being opposite to each other; and
   said pearl holder being made of opaque material and being receivable in said slots, said pearl holder having at least one notch and said aperture being optically connected to the bottom of said notch.

5. An apparatus as recited in claim 1, wherein:
   said housing includes a left side wall, a right side wall, and front and back walls, and has slots placed in said left and right side walls, said left and right side walls being opposite to each other; and
   said pearl holder being made of opaque material and being receivable in said slots, said pearl holder having a trough and said aperture being optically connected to the bottom of said trough, said trough receiving a string of pearls that can be successively positioned to said aperture.

6. An apparatus as recited in claim 1, wherein said housing includes:
   a first portion encompassing said light source and having a means for removably receiving said pearl holder; and
   a second portion encompassing said lens system.

7. An apparatus as recited in claim 6, wherein:
   said first portion and said second portion of said housing are movably secured to one another by a hinge.

8. An apparatus for measuring the thickness of the nacre coating of a cultured pearl, comprising:
   a light source;
   a lens system;
   a reticle illuminated by said light source;
   a housing having a substantially dark viewing chamber optically connected between said lens system and said light source, said substantially dark viewing chamber enclosing a cultured pearl, said housing being arranged to prevent entry of extraneous light into said substantially dark viewing chamber; and
   a pearl holder at least partially contained in said substantially dark viewing chamber, said pearl holder having first and second apertures, said first aperture being arranged to allow light from said light source to illuminate said cultured pearl, said second aperture being positioned adjacent to said first aperture and arranged to allow said reticle illuminated by said light source to be observed through said lens system.

9. An apparatus as recited in claim 8, wherein said housing includes:
   a bore optically connecting said light source and said first and second apertures of said pearl holder.

10. An apparatus as recited in claim 9, wherein:
    said reticle is at least partially located in said bore.

11. An apparatus as recited in claim 10, wherein said reticle includes a grid film.

12. An apparatus as recited in claim 11, wherein said reticle further includes:
    a light reducing film.

13. An apparatus as recited in claim 8, wherein:
    said second aperture has a diameter of about 1.6 mm.

14. An apparatus as recited in claim 11, wherein said grid film:
    grid lines, each grid having about 0.01–1.0 mm sides.

15. An apparatus as recited in claim 14, wherein each said grid has about 0.5 mm sides.

16. An apparatus as recited in claim 14, wherein:
    said lens system provides a magnification factor of about 5× to 10×.

17. A method for measuring the thickness of the nacre coating of a cultured pearl, comprising the steps of:
    (a) placing a cultured pearl in a substantially dark viewing chamber having an lens system and arranged to prevent entry of extraneous light into said substantially dark viewing chamber;
    (b) illuminating said pearl by lighting a relatively small portion of a side of said pearl with light from a light source, so that the thickness of the nacre coating of said cultured pearl is observable through said lens system;

(c) providing a reticle image observable through said lens system; and (d) measuring the thickness of the nacre coating of said pearl illuminated in step (b) by comparison with said reticle image provide in step (c).

18. A method as recited in claim 17, wherein said step of providing a reticle image observable through said lens system includes the sub-step of:

projecting said reticle image through an aperture in said dark viewing chamber, said aperture being located adjacent to said cultured pearl.

19. A method for positive identification of a natural pearl and for measuring the thickness of the nacre coating of a cultured pearl, comprising the steps of:

(a) placing a pearl in a substantially dark viewing chamber having a lens system and arranged to prevent entry of extraneous light into said substantially dark viewing chamber;

(b) illuminating said pearl by lighting a relatively small portion of a side of said pearl with light from a light source, so that luminescence is stimulated throughout said pearl only when said pearl is a natural pearl, and so that the thickness of the nacre coating of said pearl is observable through said lens system when said pearl is a cultured pearl;

(c) providing a reticle image observable through said lens system; and (d) measuring the thickness of the nacre coating of said pearl illuminated in step (b) by comparison with said reticle image provide in step (c).

20. A method as recited in claim 19, wherein said step of providing a reticle image observable through said lens system includes the sub-step of:

projecting said reticle image through an aperture in said substantially dark viewing chamber, said aperture being located adjacent to said pearl.

* * * * *